(12) United States Patent
Wolfson et al.

(10) Patent No.: US 6,740,343 B2
(45) Date of Patent: May 25, 2004

(54) STANDARDIZED EXTRACTS OF SCUTELLARIA LATERIFLORA

(75) Inventors: Philip E. Wolfson, San Anselmo, CA (US); David Ludwig Hoffmann, Santa Rosa, CA (US)

(73) Assignee: Phytos, Inc., San Anselmo, CA (US)

( * ) Notice: Subject to any disclaimer, the term of this patent is extended or adjusted under 35 U.S.C. 154(b) by 0 days.

(21) Appl. No.: 10/244,811

(22) Filed: Sep. 17, 2002

(65) Prior Publication Data

US 2003/0054050 A1 Mar. 20, 2003

Related U.S. Application Data

(60) Provisional application No. 60/323,048, filed on Sep. 17, 2001.

(51) Int. Cl.[7] .............................................. A61K 35/78
(52) U.S. Cl. ........................................ 424/741; 424/725
(58) Field of Search .......................................... 424/741

(56) References Cited

U.S. PATENT DOCUMENTS 6,200,594 B1 * 3/2001 Ernest et al.

OTHER PUBLICATIONS

Nishikawa et al. (Natural Medicines (1999), vol., 53, No. 4, pp. 209–213).*

Medina, et al., Overview Flavonoids: A new family of benzodiazapine receptor ligands. *Neurochem Res.* 1997 22(4) :419.

* cited by examiner

Primary Examiner—Leon B. Lankford, Jr.
Assistant Examiner—Susan D. Coe
(74) Attorney, Agent, or Firm—Richard C. Litman

(57) ABSTRACT

The present invention relates to an improved extract of *Scutellaria lateriflora*, a method of preparing the same, and a pharmaceutical composition prepared from the present extract suitable for treating anxiety, insomnia, convulsions, muscle tension and spasm, and related manifestations and disorders in humans and other mammals. The invention also relates to an improved method of treating anxiety, insomnia, convulsions, muscle tension and spasm, and related manifestations and disorders in humans and other mammals by administering the improved extract of *Scutellaria lateriflora*.

6 Claims, 2 Drawing Sheets

STANDARDIZED EXTRACTS OF *SCUTELLARIA LATERIFLORA*

CROSS-REFERENCE TO RELATED APPLICATION

This application claims the benefit of U.S. Provisional Patent Application Serial No. 60/323,048, filed Sep. 17, 2001, entitled "Process and Total Phenol Standardization for Blue Skullcap (*Scutellaria lateriflora*)".

FIELD OF THE INVENTION

The present invention is related to novel standardized extracts of *Scutellaria lateriflora*; methods for preparing the same; compositions containing these standardized extracts; and the treatment of anxiety, insomnia, convulsions, muscle tension and spasm, and related manifestations and disorders in humans and other mammals through the administration of compositions containing these standardized extracts.

BACKGROUND OF THE INVENTION

Anxiety is one of the most frequent psychological problems that humans experience. It is estimated that anxiety related psychiatric disorders affect over 13% of the population each year in the United States. The cost of this individual suffering and the social burden of anxiety are significant. Effective treatment of anxiety and related disorders can significantly alleviate the suffering and distress associated with such disorders.

Treatment of anxiety and the related conditions of insomnia and convulsions is as old as recorded history, and the interventions are encyclopedic. While there are effective treatments, there is much need for improvement. The search for new anxiolytic medicines that meet acceptable standards of efficacy and safety continues.

In recent years this search has broadened to include an assessment of herbal sedatives and anxiolytics. These have been used in both folk medicine and phytotherapy for centuries, and continue to have widespread use in many cultures.

*Scutellaria lateriflora*, also known as Blue Skullcap or American Skullcap, (hereinafter *S. lateriflora*) is a perennial herb indigenous to North America and Europe. Long used as a traditional herbal remedy for a variety of indications, it is known to exhibit anxiolytic, sedative, and anticonvulsant effects. The use of *S. lateriflora* to treat anxiety, insomnia and related disorders has been one of its major therapeutic applications. The herb is typically used in the form of teas and tinctures. It can also be ingested in fresh or dried forms.

The leaves, stems and flowers of *S. lateriflora* contain a number of biologically active compounds. Nishikawa, et al. analyzed *S. lateriflora*, and found the principle phenolics in leaves, stems, and roots were baicalein and wogonin (Nishikawa, et al. Phenolics in tissue cultures of Scutellaria. *Natural Medicines* 53:209–213, 1999). Gafner, et al. screened dried aboveground parts of *S. lateriflora* and identified the flavones baicalin and baicalein, as well as 5,6,7-trihydroxy-2'-methoxyflavone and its 7-0-glucuronide. (Analysis of *Scutellaria lateriflora* and its adulterant *Teucrium canadense* by HPLC-UV and HPLC-UV/MS, Tom's of Maine, PO Box 710, Kennebunk, Me. 04043, USA). Finally, a number of the flavones found in *S. lateriflora* have been reported to selectively bind with high affinity to central benzodiazepine receptor sites, leading to the view that the flavones exerts powerful anxiolytic and other benzodizepine effects in rats. (Medina, et. al., Overview-Flavonoids: A new family of benzodiazapine receptor ligands. *Neurochem Res.* 1997 22(4):419.)

While the prior art identifies certain compounds in *S.lateriflora*, it has not been demonstrated which compounds are therapeutically effective. Further, none of the known *S. lateriflora* extracts are standardized. In addition, the currently available commercial *S. lateriflora* preparations do not have adequate therapeutic effects, principally because concentrations of the therapeutically effective components are too low or are not sufficiently bioavailable.

There is a great need, therefore, for extracts of *S. lateriflora* that have rigorous standardization based on the presence of specific markers, and good quality control. There is also a need for extracts of *S. lateriflora* that have higher levels of therapeutically active components, better bioavailability, and demonstrated therapeutic efficacy. Further there is a need for methods of preparing these extracts, as well as for compositions containing these extracts. There is also a need for treatments for anxiety, insomnia, convulsions, muscle tension and spasm, and related manifestations and disorders using these extracts.

SUMMARY OF THE INVENTION

The present invention is directed generally to novel standardized extracts of *Scutellaria lateriflora* for the treatment of symptoms of anxiety, insomnia, convulsions, muscle tension and spasm, and related manifestations and disorders in humans and other mammals.

The present invention is further directed to methods of preparing such extracts.

In one particular aspect of the present invention, there is provided an extract of *S. lateriflora* which comprises an active component for treatment of symptoms of anxiety, insomnia, convulsions, muscle tension and spasm, and related manifestations and disorders that includes at least one specific phenolic marker in an amount of at least 8% by weight based on the total weight of the extract.

In another particular aspect of the present invention, there is provided a method of preparing the extract, which comprises:
treating a mass of *S. lateriflora* with a solvent suitable for extracting at least one active phenolic component to yield an extract solution;
concentrating the extract solution to an extent necessary to provide a minimum desirable concentration of the active component for the treatment of anxiety, insomnia, convulsions, muscle tension and spasm, and related manifestations and disorders, and;
standardizing the extract to yield a known amount of at least one specific phenolic marker.

The present invention is further directed to a pharmaceutical composition useful for treating anxiety, insomnia, convulsions, muscle tension and spasm, and their related manifestations and disorders, comprising as an active component an effective amount of at least one specific phenolic marker extracted from *S. lateriflora*, and a pharmaceutically acceptable carrier, and methods of using the same.

The present invention is further directed to methods of treating anxiety, insomnia, convulsions, muscle tension and spasm, and their related manifestations and disorders by administering the novel standardized extracts of this invention.

BRIEF DESCRIPTION OF THE DRAWINGS

The following drawings are illustrative of embodiments of the present invention and are not intended to limit the invention as encompassed by the claims forming part of the application.

DETAILED DESCRIPTION OF THE INVENTION

The present invention provides highly effective standardized extracts of *Scutellaria lateriflora* for the treatment of anxiety, insomnia, convulsions, muscle tension and spasm, and their related manifestations and disorders in humans and other mammals. The invention is further directed to methods of preparing these extracts from *S. lateriflora* for the treatment of anxiety, insomnia, convulsions, muscle tension and spasm, and related manifestations and disorders in humans and other mammals. Further, the present invention provides compositions for the treatment of anxiety, insomnia, convulsions, muscle tension and spasm, and related manifestations and disorders in humans and other mammals containing the inventive standardized extract of *S. lateriflora*, and methods of treating these disorders by administering these compositions.

The spectrum of conditions for which the inventive extract can be used include but are not limited to:

a) The spectrum of anxiety disorders in adolescents and adults including but not limited to acute anxiety reactions, general anxiety disorder, obsessive compulsive disorder, agoraphobia with and without panic attacks, acute and chronic post-traumatic stress disorder, social phobia, and adjustment disorders.

b) The spectrum of dysphoric disorders, mood disorders that are accompanied by anxiety and insomnia, including pre-menstrual dysphoric disorder (PMDD) and depression accompanied by anxiety.

c) The spectrum of sleep disorders.

d) The spectrum of sexual disorders in which anxiety may play a role.

e) The spectrum of drug or substance abuse related disorders in which anxiety may play a role f) The spectrum of somatic disorders in which anxiety may play a role including headaches, irritable bowel syndrome, and various somatization disorders.

g) Headache.

h) The spectrum of symptoms of anxiety including irritability, fearfulness, agitation, anger, compulsive behaviors, obsessive thoughts, irritability related to the menstrual cycle, marital discord, occupational, and social and educationally related anxiety.

i) Muscle tension and spasm.

j) Convulsive disorders such as petit mal.

k) Other similar or related conditions known to those skilled in the art.

The foregoing disorders, separately or in combination, and related manifestations and disorders are herein referred to as "*S. lateriflora* responsive disorders."

Figure 1:
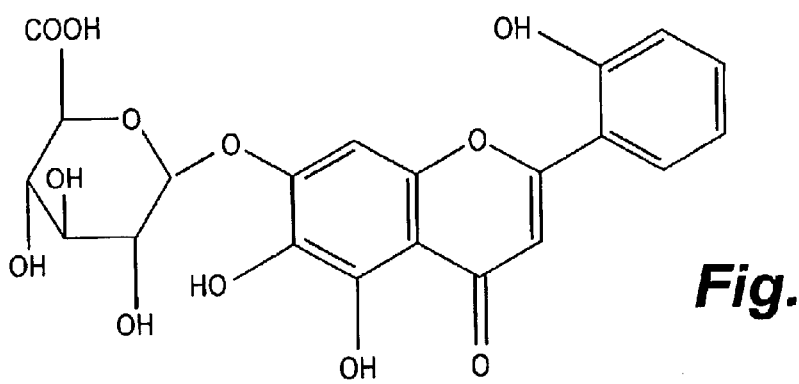
FIG. 1 shows the chemical structure of Scutellarin.
Figure 2:
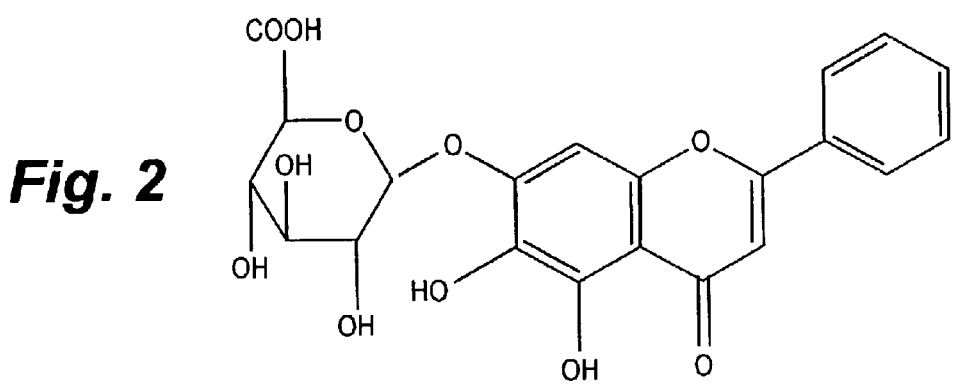
FIG. 2 shows the chemical structure of Baicalin.
Figure 3:
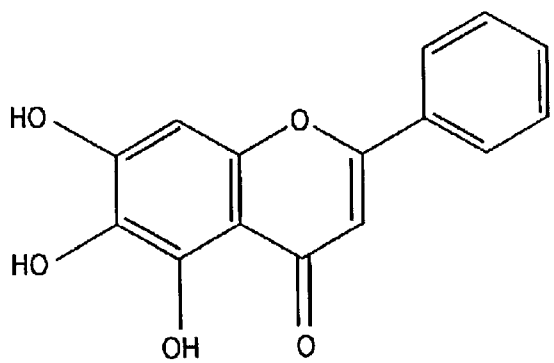
FIG. 3 shows the chemical structure of Baicalein.
Figure 4:
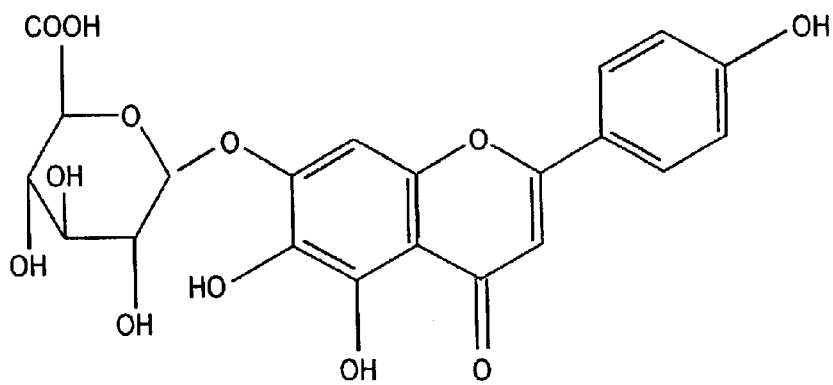
FIG. 4 shows the chemical structure of Ikonnoside A.

*S. lateriflora* is a perennial herb. The flowers, leaves, and stems of *S. lateriflora* can be used for obtaining extracts that are effective for treating *S. lateriflora* responsive disorders. These therapeutically effective extracts include at least one phenolic compound. These phenolic compounds include, but are not limited to, scutellarin (FIG. 1), baicalin, (FIG. 2) baicalein (FIG. 3), 5,6,7-trihydroxy-2"-hydroxyflavone (hereinafter "IkonnosideA") (FIG. 4), scutellarein, wogonin, 5,6,7-trihydroxy-2'-methoxyflavone-7-O-glucuronide, and 5,6,7-trihydroxy-2'-methoxyflavone. These phenolic compounds can be identified and quantified in this invention. Each of these compounds is defined herein as a "specific phenolic marker." The group comprising at least one phenolic compound, including but not limited to one specific phenolic marker, is defined herein as "total phenolics."

A novel aspect of this invention is the standardization of the total phenolics, specific phenolic markers, and the entire extract. The standardized extracts of this invention have several advantages compared to current *S. lateriflora* extracts. They have better batch-to-batch consistency, leading to more predictable safety and efficacy profiles. They have better bioavailability. They also have higher amounts of at least one specific phenolic marker. The inventive extracts can be standardized according to at least one assay. The extracts can be standardized by quantifying the concentration of total phenolics. The extracts can also be standardized by quantifying the concentration of specific phenolic markers. The entire extract can also be standardized by assaying its biological activity, as measured by the affinity of the extract for the gamma amino butyric acid-A agonist site ("GABA-A agonist site) in neuronal tissue.

Unless specified otherwise, the term "% by weight" as used herein with reference to the inventive standardized extract or composition, denotes the percent of the total weight of the inventive extract contributed by the active component. This theoretical value can differ from the experimental value, because in practice, the extract or composition typically may retain some of the water and/or other substances such as alcohols (e.g., ethanol) that may be used in preparing the final product. In addition, the chemical composition of the plant material from a particular plant may vary with, for example, the conditions under which the plant is grown (e.g., soil or climate). A particular compound or mixture of compounds can exhibit pharmacological activity over a readily ascertainable range of compositions and dosages. Therefore it will be understood that the percentages by weight recited throughout are meant to include such variations outside the stated percentages or percentage ranges as would be expected by one skilled in the art.

In particular, the present invention relates to a standardized extract of *S. lateriflora*, which comprises at least one specific phenolic marker (i.e. "total phenolics"), in an amount of at least 8% by weight based on the total weight of the extract. In a more preferred embodiment of the present invention, the total phenolics are present in an amount of at least 12% by weight. In a most preferred embodiment of the present invention, the total phenolics are present in an amount of at least 16% by weight.

Total phenolics are assayed using the Folin-Ciocalteu ("FC") method. This assay measures the concentration of total phenolics spectrophotometrically. The standard used in this assay includes, but is not limited to, gallic acid. This is a colorimetric redox assay that measures all phenolic molecules, with no differentiation between gallic acid or another standard, monomers, dimers and larger phenolic compounds. Results are typically expressed as equivalents to the standard (e.g. "gallic acid equivalents"). This method has been used in the wine industry for over 30 years. The first paper on this method was published in 1927. In 1965

Singleton and Rossi improved the reproducibility of the assay. The FC method is known to those skilled in the art.

The present invention further relates to an extract that has been standardized based on the concentration of individual specific phenolic markers. In one embodiment the specific phenolic markers are scutellarin, baicalin, baicalein, and Ikonnoside A.

In a preferred embodiment of this invention the extract contains at least 0.30% by weight scutellarin; at least 2.50% by weight baicalin; at least 1.20% by weight baicalein; and at least 0.35% by weight Ikonnoside A.

In a more preferred embodiment of this invention the extract contains at least 0.60% by weight scutellarin; at least 5.00% by weight baicalin; at least 1.80% by weight baicalein; and at least 0.80% by weight Ikonnoside A.

In the most preferred embodiment of this invention the extract contains at least 1.00% by weight scutellarin; at least 8.00% by weight baicalin; at least 2.20% by weight baicalein; and at least 1.30% by weight Ikonnoside A.

Specific phenolic markers are assayed using High Performance Liquid Chromatography ("HPLC"). One example of this assay is described in Gafner et al. HPLC is known to those skilled in the art.

The present invention further relates to an extract that has been standardized for its biological activity. This is measured by the binding of the extract at the GABA-A agonist site on the GABA-A receptor of neuronal tissue. Gamma-amino-butyric-acid ("GABA") is the primary inhibitory neurotransmitter in the human brain. The GABA-A receptor is a membrane protein that functions as a ligand-gated chloride ion channel in the neuronal membrane. Opening this chloride ion channel inhibits neuronal firing.

The GABA-A agonist site is one of several binding sites on the GABA-A receptor. The inventors have surprisingly found that the S. lateriflora extract of this invention has a high binding affinity at GABA-A agonist site. This is consistent with the anxiolytic properties of the extract.

The biological activity of the extract can be measured, and the extract standardized, using a standard Radio Ligand Assay to measure GABA-A receptor binding activity. Results are reported as Ki, the equilibrium dissociation constant for S. lateriflora extract binding to the GABA-A receptor in the presence of muscimol. The Radio Ligand Assay technique is known to those skilled in the art.

The extracts of this invention can be standardized using at least one of the previously described standardization assays.

The present invention further relates to a method of preparing an extract from the mass comprised of stems, flowers and leaves of S. lateriflora. This mass is subjected to an extraction process that is effective in concentrating at least one specific phenolic marker. The extract is then dried. The extract is then standardized according to the invention. The extract can further be combined with fillers, excipients, binders and the like to form a composition suitable for administration for the treatment of S. lateriflora responsive disorders.

The extraction process uses a suitable solvent selected from water, and organic solvents with or without water. Suitable organic solvents include but are not limited to non-toxic aqueous or non-aqueous monohydric or polyhydric alcohols, hexane, methylene glycol, glycerin, and similar solvents known to those in the art. Other extraction methods such as use of super-critical $CO_2$ may also be used. Preferably an aqueous solvent having at least 10% volume/volume ("v/v") of an alcohol is used in the extraction, more preferably at least 30% v/v of an alcohol, and most preferably at least 50% v/v of an alcohol. The preferred alcohol is ethanol.

The extraction process may be carried out using methods known in the art, including but not limited to solvent extraction, percolation, vat extraction, or countercurrent extraction. The degree of comminutation of the plant material prior to the extraction process should provide sufficient particulate surface for the extraction solvent to contact the material. Other extraction methods are known to those skilled in the art. Extraction may be at ambient temperature or at elevated temperature. The resulting extract solution is then dried to substantialy remove the solvent.

The inventors have discovered that the concentration of total phenolics as well as certain specific phenolic markers is increased if the plant mass is freeze-dried after harvesting and before extraction or processing. In a preferred embodiment of the invention, therefore, the stems, leaves, and flowers of S. lateriflora are freeze-dried before extraction. Freeze-drying can be done immediately upon harvesting the plant. Or the harvested plant can immediately be frozen and then freeze-dried within at least 30 days.

In one embodiment of the invention the extraction steps are as follows:

a) S. lateriflora is harvested during the early flowering season, when the amount of at least one specific phenolic marker is at its peak.
b) The stems, flowers, and leaves of the plant are immediately frozen to prevent fermentation, or are immediately freeze-dried. The frozen plant mass is freeze dried within one month of harvest. Freeze-drying is done at minimal heat.
c) The freeze-dried material is pulverized to optimal particle size for percolation extraction.
d) The pulverized material is then extracted and solid material is removed using the percolation method of extraction, in an ethanol/water solution wherein the ethanol is preferably 10% v/v, more preferably 30% v/v, and most preferably 50% v/v.
e) The resulting extract is then dried and concentrated.
f) The extract is then assayed for at least one of the following: amount of total phenolics; amounts of specific phenolic markers; binding of the extract at the GABA-A agonist site of the GABA receptor in-neuronal tissue.

The extracts obtained have at least 8% by weight total phenolics, preferably at least 12% by weight total phenolics, and most preferably at least 16% by weight total phenolics.

The extracts obtained preferably have at least 0.30% by weight scutellarin, at least 2.50% by weight baicalin, at least 1.20% by weight baicalein, and at least 0.35% by weight Ikonnoside A.; preferably at least 0.60% by weight scutellarin, at least 5.00% by weight baicalin, at least 1.80% by weight baicalein, and at least 0.80% by weight Ikonnoside A; and most preferably at least 1.00% by weight scutellarin, at least 8.00% by weight baicalin, at least 2.20% by weight baicalein, and at least 1.30% by weight Ikonnoside A.

Preferably the extracts obtained bind to the GABA-A agonist site of the GABA-A receptor in mammalian neuronal tissue.

In accordance with this invention, the extract can be included in the preparation of pharmaceutical compositions containing a sufficient concentration of the extract to achieve a desirable pharmaceutical effect within an acceptable dosage regimen. All the compositions can be standardized for total phenolics and specific phenolic markers by varying the amount of standardized extract added during the compounding process. The S. lateriflora extracts of the invention can be processed in the usual way for the preparation of pharmaceutical compositions, including but not limited to tablets, controlled-release products, capsules, caplets, solutions, and the like. The pharmaceutical composition can also be formulated as confections including but not limited to gums, lozenges, troches and the like. One preferred composition is as a tablet containing between 50–300 mg of the inventive extract, and more preferably containing 100–200 mg of the inventive extract.

The composition formulated as tablets, controlled-release products, capsules, caplets, solutions, and the like further includes, but is not limited to, diluents, binders, lubricants, disintegrants, colors, flavors, and the like. Non-limiting examples of diluents include dicalcium phosphate, calcium sulfate, mannitol, sorbitol, and the like. Non-limiting examples of binders include starch, and sugars such as sucrose, glucose and dextrose. Non-limiting examples of lubricants include talc, starch, paraffin, stearic acid, magnesium stearate, and calcium stearate. Non-limiting examples of disintegrators include corn and potato starch, methylcellulose, agar, and bentonite. Non-limiting examples of coloring agents include any of the approved certified water-soluble FD&C dyes and mixtures of the same. Compounding the inventive composition to a suitable pharmaceutical composition is known to one skilled in the art.

The pharmaceutical composition can also be formulated as a confection such as a gum, lozenge, troche, and the like. Components that may be incorporated into a confection include but are not limited to sweeteners, coloring agents, flavoring agents, preservatives, diluents, emulsifying agents, excipients, and the like.

Suitable sweeteners may be readily selected by those skilled in the art, and the amount of sweetener to be determined by taste. The sweetener may be naturally occurring or synthetic, and may be nutritive or non-nutritive. Examples of such sweeteners include, but are not limited to, the saccharides, sugar alcohols such as alcohol and mannitol, water-soluble artificial sweeteners such as soluble saccharine salts, and dipeptide-based sweeteners such as L-aspartyl-L-phenylalanine methyl ester.

Suitable colorants include dyes that are generally suitable for food, drug and cosmetic applications, i.e., those known as F.D.&C. dyes.

Flavorings may include natural or artificial flavors such as mint oils, citrus oils, and the like.

The composition may be prepared as a gum using conventional means. The "gum base" may be one a number of types of compositions, typically prepared by heating and blending various ingredients, e.g., natural gums, synthetic resins, waxes, and the like. Waxes, including natural and synthetic waxes, petroleum waxes, paraffin waxes and microcrystalline waxes may also be incorporated into the gum base.

Lozenges will typically be shaped solids containing the extract in a candy or glycerinated base. Preparation of lozenge forms is well known in the art.

The most preferred composition is a controlled-release formulation. Controlled-release formulations may employ alginates, microcrystalline cellulose, cellulose ethers, vegetable gums, and polymer complexes to sustain the extract in the system. Physical means such as coating, microencapsulation, and embedding in complex matrices may be employed for this purpose. A preferred physical means is microencapsulation.

Other techniques known in the art can also be used to produce a controlled release composition. The controlled release composition yields an immediate release of effective dosage, and a sustained release such as to yield an effective dosage duration ranging from 3–6 hours, preferably 3.5 to 4.5 hours. A sustained release composition provides the benefit of reducing the total amount of pharmacologically active material necessary for relief of the symptoms of anxiety and/or insomnia, etc.

The present invention provides a method for treatment of anxiety based disorders and symptoms thereof comprising the administration of an effective amount of the inventive *S. lateriflora* extract. The extract may be administered at a dosage level of from 1 to 2 tablets containing a specified amount of the extract based on standardization using the three methods for standardization as described herein. Administration may be repeated every 4 to 5 hours as needed and at bedtime, this for adults. The exact dosage will vary according to the patient to be treated and will depend on such factors such as requirements of the patient, the severity of the disorder or condition being treated and the age and health of the person being treated, as well as use of other medications and herbal remedies. The determination of optimum dosages can be made for a particular patient by one skilled in the art.

The following examples illustrate the invention.

EXAMPLES

In Examples 1–5 below, all or some of the following samples were studied:

Sample 1: *S. lateriflora* was harvested at peak flowering. The plant mass contained minimal stems. The plant mass was freeze-dried within hours of harvest. The freeze-dried mass was assayed for total phenols (Ex. 1), and encapsulated in 100 mg capsules for use in Ex. 5.

Sample 2: *S. lateriflora* was harvested at peak flowering. Flowering tops, leaves, and stems were frozen. The frozen material was extracted with a water/ethanol solution of 25% ethanol by volume. The percolation extraction method was used. The extracted mass was then freeze-dried.

Sample 3: *S. lateriflora* was harvested at peak flowering. Flowering tops, leaves, and stems were frozen. The frozen plant mass was freeze-dried. The freeze-dried material was extracted with a water/ethanol solution of 40% ethanol by volume and then dried.

Sample 4: *S. lateriflora* was harvested at peak flowering. Flowering tops, leaves, and stems were frozen. The frozen plant mass was freeze-dried. The freeze-dried material was extracted with a water/ethanol solution of 80% ethanol by volume and then dried.

Example 1

Materials and Methods:

Extracts of *S. lateriflora* were prepared and assayed using the Folin-Ciocalteu ("FC") method.

The FC reagent is an oxidizing agent comprised of heteopolyphosphotungstate-molybdate. The blue colored product is a mixture of the 1-, 2-, 4- and 6-electron reduction products in the tungstate series $P_2W_{18}O_{62}-7$ to $H_4P_2W_{18}O_{62}$ and the 2-, 4- and 6-electron reduction products in the molybdate series $H_2P_2Mo_{18}O_{62}-6$ and $H_6P_2Mo_{18}O_{62}-6$.

Results:

| Sample | % Total phenols |
|--------|-----------------|
| 1 | 9.4* |
| 2 | 7.32** |
| 3 | 12.5%** |
| 4 | 18.8%** |

*Standardized to gallic acid
**Standardized to chlorogenic acid

It is believed that the level of total phenols in Sample 1 is higher than in Sample 2 because the harvested mass in Sample 1 was freeze-dried, whereas the extraction process for Sample 2 did not include freeze drying before extraction.

Example 2

Materials and Methods:

Samples of extract 2 and 4 were assayed for specific phenolic markers. The assay procedure was as follows: Samples 2 and 4 were completely dissolved by sonication (15 min.) in 10 mL 60% ethanol. The clear solution was directly injected in the HPLC. The HPLC system had the following specifications: Standard C-18 column (250×4.6 mm. I.D.; 5 µm) with a C-18 guard column; MeCN (0.05% TFA)-H2O ((0.05% TFA) gradient; Detection: UV at 280 nm.

Results:

|           | Compound | Mean [%] | Stdev [%] |
|-----------|----------|----------|-----------|
| Sample 2: | Scutellarin | 0.264 | 0.005 |
|           | Baicalin | 2.330 | 0.030 |
|           | Baicalein | 1.069 | 0.001 |
|           | Ikonnoside A* | 0.326 | 0.002 |
| Sample 4: | Scutellarin | 0.394 | 0.050 |
|           | Baicalin | 4.994 | 0.556 |
|           | Baicalein | 2.808 | 0.208 |
|           | Ikonnoside A | 0.338 | 0.036 |

Example 3

Materials and Methods:

A bioassay of Sample 2 for GABA-A agonist receptor binding was done. A Standard Radio Ligand assay was used. Reference standards were run as an integral part of each assay to ensure the validity of the results obtained. A 15-receptor screen was conducted, which included adenosine A1, adenosine transporter, adrenergic alpha1, alpha2, and beta, cannabinoid CB1, cb2, GABA transporter, GABA-A agonist, GABA-B, GABA-A denzodiazapine, flutamate, histamine H1, mu opioid, nonselective opioid, and 5HT-2A.

Results:

The Sample 2 S. lateriflora preparation produced 84% inhibition of binding of a 1 nanomolar preparation of the high-affinity GABA-A ligand muscimol with rat-brain membrane. There was no significant binding activity at any other site. The Ki was 2.32 µM. The Ki was calculated using the equation of Chang and Prusoff (Chang, Y, Prosoff, W. H., Biochem. Pharmacol. 22:3099–3108, 1973) using the observed IC50 of the tested compound, the concentration of radioligand employed in the assay, and the historical values for the Kd of the ligand.

Example 4

Materials and Methods:

A toxicological assessment of a concentrated standardized extract of S. lateriflora was conducted to determine LD50.

Five male and five female rats were fasted for approximately 21 hours. After the fasting period, 5 g/kg of Sample B was administered as a 40% w/w suspension in a 1% w/w solution of carboxymethylcellulose in distilled water. The animals were observed for mortality, signs of gross toxicity, and behavioral changes at approximately one and three hours post dosing, and at least once daily for 14 days. Body weights were recorded prior to induction and at termination. All animals were euthanized by CO2 inhalation.

Results:

All animals survived, gained weight, and appeared active and healthy. There were no signs of gross toxicity, adverse pharmacologic effects, or abnormal behavior.

This study validates the safety of the standardized extracts for human use at the levels claimed in this application.

Example 5

Materials and Methods

A study was conducted to measure the effects of various preparations of S. lateriflora on energy, cognition and anxiety. A placebo-controlled, double-blind crossover design was used.

Test subjects were nineteen healthy volunteers (15 female and 4 male) ranging in age from 20–70. Exclusion criteria were a history of drug and/or alcohol abuse, concommitant and current ongoing treatment with other prescription or herbal medications, pregnancy, lactation, and participation in another study within the previous 30 days.

Each subject was supplied with separately coded packets of four different preparations. The four test preparations were:

A. Two capsules of placebo, indistinguishable from test products.
B. One capsule of 350 mg of an organically grown and freeze-dried S. lateriflora product supplied by Eclectic Institute, Oregon.
C. One 100 mg gelatin capsules of extract of S. lateriflora prepared according to inventive Sample 1, described above.
D. Two capsules (i.e. 200 mg) of test preparation C.

Subjects took one dose of each test preparation on separate days within a two week period in their own settings, without the observation of the clinical investigators. There was at least one non-treatment day between treatments. Subjects evaluated the effect of the four different treatments on anxiety, cognition and energy at 30 minute intervals for the first 120 minutes after administration. Subjects rated their experience of the outcome variables on an ordered categorical scale ranging from "Relaxed" to "Tense" for anxiety level; "Diminished" to "Increased" for cognition; and "Sedating" to "Stimulating" for energy level.

Data was sorted by treatment condition and time point for each of the 3 treatment variables. Differences from baseline were computed for each subject. The mean differences and standard deviations for each treatment condition over time were calculated and plotted.

Results

Figure 5:
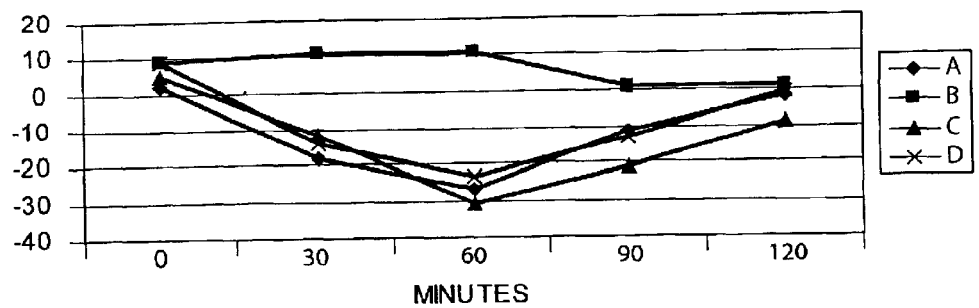
FIG. 5 is a graph showing the effect on anxiety of a placebo and 3 formulations of *S. lateriflora*.
Figure 6:
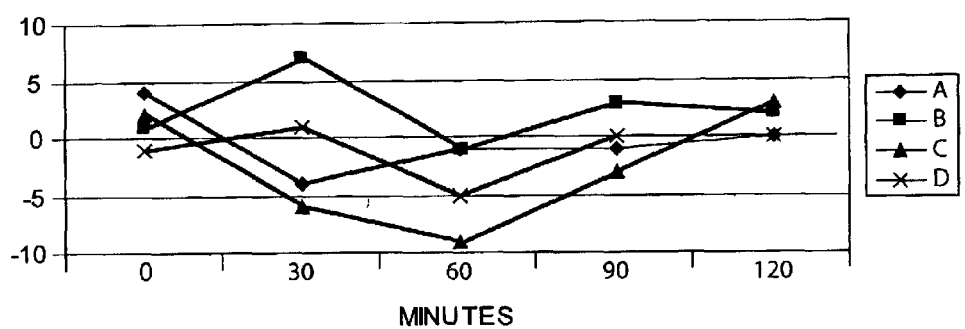
FIG. 6 is a graph showing the effect on cognition of a placebo and 3 formulations of *S. lateriflora*.
Figure 7:
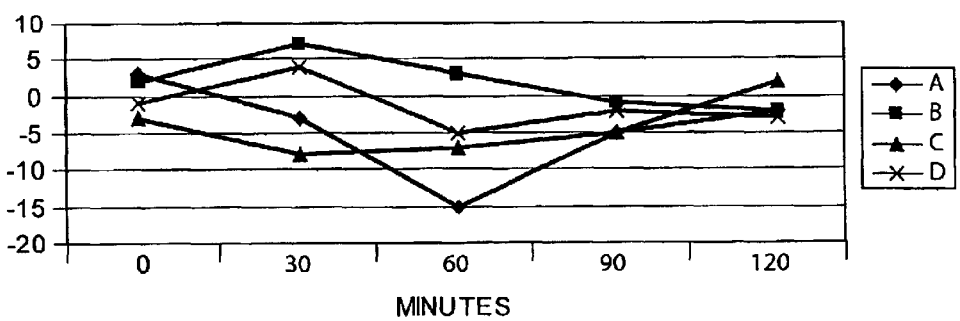
FIG. 7 is a graph showing the effect on energy of placebo and 3 formulations of *S. lateriflora*.

The results are shown in FIGS. 5, 6, and 7. The effect on anxiety, FIG. 5, was most pronounced. Inventive Sample D had the greatest anxiolytic compared to placebo and baseline, and inventive Sample B and Sample C were similar in the degree of their anxiolytic effects compared to placebo. Inventive Samples C and D had a lesser impact on energy and cognition.

The data clearly indicate an anxiolytic effect for the inventive extracts. Additionally, these products did not significantly impair cognition or energy.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A standardized extract of *Scutellaria lateriflora* for the treatment of anxiety, insomnia, convulsions, muscle tension, and spasm in humans and other mammals, said extract comprising at least 0.30% by weight scutellarin; at least 2.50% by weight baicalin; at least 1.20% by weight baicalein; and at least 0.35% by weight Ikonnoside A.

2. The extract of claim 1 comprising at least 0.60% by weight scutellarin; at least 5.00% by weight baicalin; at least 1.80% by weight baicalein; and at least 0.80% by weight Ikonnoside A.

3. The extract of claim 1 comprising at least 1.00% by weight scutellarin; at least 8.00% by weight baicalin; at least 2.20% by weight by baicalein; and at least 1.30% by weight Ikonnoside A.

4. A pharmaceutical composition for the treatment of anxiety, insomnia, convulsions, muscle tension and spasm, in humans and other mammals, said composition comprising an extract of *Scutellaria lateriflora* containing at least 0.30% by weight scutellarin; at least 2.50% by weight baicalin; at least 1.20% by weight baicalein; and at least 0.35% by weight Ikonnoside A.

5. The pharmaceutical composition of claim 4, wherein said extract of *Scutellaria lateriflora* contains at least 0.60% by weight scutellarin; at least 5.00% by weight baicalin; at least 1.80% by weight baicalein; and at least 0.80% by weight Ikonnoside A.

6. The pharmaceutical composition of claim 4, wherein said extract of *Scutellaria lateriflora* contains at least 1.00% by weight scutellarin; at least 8.00% by weight baicalin; at least 2.20% by weight baicalein; and at least 1.30% by weight Ikonnoside A.

* * * * *